United States Patent [19]

Langer et al.

[11] Patent Number: 4,650,465

[45] Date of Patent: Mar. 17, 1987

[54] INJECTORS AND INJECTOR CONSOLES

[75] Inventors: Alois A. Langer, Forest Hills; Albert W. Rinne, Bethel Park, both of Pa.

[73] Assignee: Liebel-Flarsheim Company, Cincinnati, Ohio

[21] Appl. No.: 670,685

[22] Filed: Nov. 13, 1984

[51] Int. Cl.$^4$ ............................................. A61M 5/00
[52] U.S. Cl. .............................. 604/65; 128/DIG. 12; 128/DIG. 13
[58] Field of Search ............... 128/DIG. 12, DIG. 13, 128/654; 604/65, 67, 235

[56] References Cited

U.S. PATENT DOCUMENTS

| | | | |
|---|---|---|---|
| 4,105,028 | 8/1978 | Sadlier et al. | 128/DIG. 13 X |
| 4,196,730 | 4/1980 | Wilson | 128/DIG. 12 |
| 4,237,878 | 12/1980 | Kobayashi et al. | 128/DIG. 13 |
| 4,314,484 | 2/1982 | Bowman | 128/DIG. 13 |
| 4,373,527 | 2/1983 | Fislhell | 128/DIG. 13 |
| 4,395,259 | 7/1983 | Prestele et al. | 128/DIG. 13 |
| 4,537,561 | 8/1985 | Xanthopoulos | 128/DIG. 12 |

FOREIGN PATENT DOCUMENTS 2463623  4/1981  France .................. 128/DIG. 13

Primary Examiner—Edward M. Coven
Attorney, Agent, or Firm—Marjama & Pincelli

[57] ABSTRACT

An angiographic injector having a separable console selecting and displaying injector functions and parameters. Microprocessors provide serial data transmission between console and injector base, and between injector head and injector base. A microprocessor in the base controls the injector.

5 Claims, 4 Drawing Figures

INJECTORS AND INJECTOR CONSOLES

This invention relates to injectors and injector consoles, an injector being a motor-operated device for injecting liquids for diagnostic, therapeutic, or like purposes, into the vascular system of a living being. Such devices normally have a console which is used by the operator to set injector parameters, to select injector functions and to begin and carryout injections. Prior art injectors have visually-cluttered consoles, due to the wide variety of switches, knobs, dials, etc., present thereon.

According to the present invention, such clutter is obviated by the use of a single display tube, or equivalent display means, by means of which substantially all the visual information needed by the operator will be available to him or her. At the same time, the display tube, in conjunction with injector function selectors, provides for increasing the number of selectable functions without there being a corresponding increase in the number of selectors.

In addition, these prior art consoles are also more or less inseparably integrated with the largely electronic hardware for controlling, monitoring, etc., the injector functions. Consequently, while there is the practical possibility of having the injector head (the essence of which is a motor-operated syringe) separable from the remainder of the injector in order to be able to have more leeway in locating and/or positioning the head, than the usual articulated cantilever support arm allows, about all that can be offered by way of remote control of the prior art injector is a remote start switch which is on a more or less lengthy cord and which allows the operator to locate himself at positions which are relatively freely chooseable by him and variably located with respect to the console, etc.

According to the present invention, externally-available aspects of the console, namely, display, switches, and the like, are separate from the essential, functional electronic hardware of the injector, and the linkage between hardware is effected by serial data transmission between console and hardware. Likewise, serial data transmission provides the information linkage between injector head and hardware. The serial link requires that there be only a few actual conductors between console and the rest of the injector, so now it becomes practical to locate the entire console at a nearly limitless distance from the rest of the injector.

FIG. 1 shows an injector console layout L according to the invention as it effectively appears to the operator. Thus, there is a vacuum fluorescent display tube 1, or equivalent display device, which is constructed and arranged to display two horizontal lines, each having forty characters and extending for substantially the entire width of display tube 1.

Figure 1:
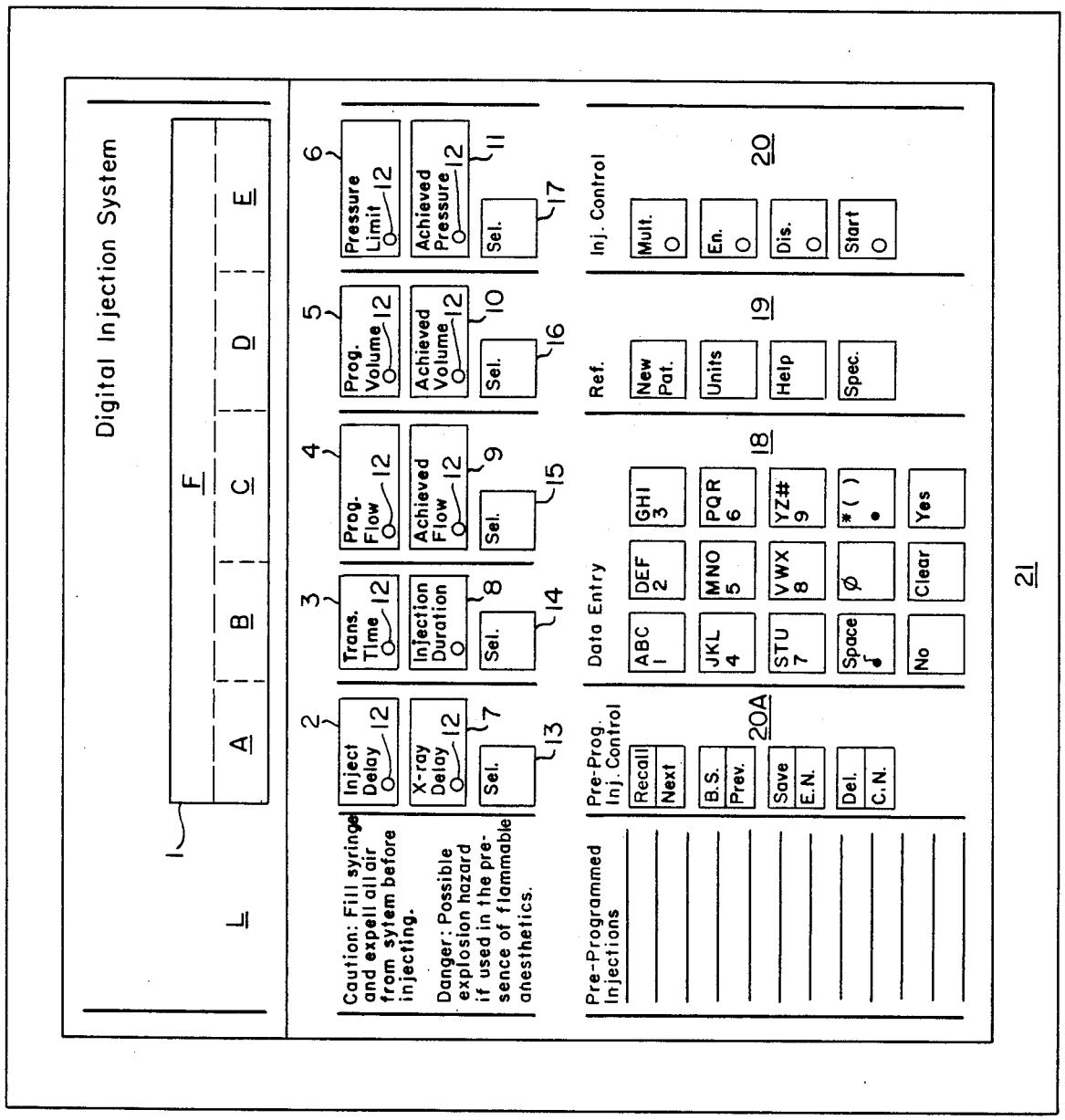
FIG. 1 shows the layout of an injector console according to the invention.

Just below the display tube 1, and parallel and substantially coextensive with display tube 1, is a set of function identifying labels 2 through 5, and below these, and parallel and substantially coextensive therewith are function identifying labels 7 through 11. Each of the labels has a LED 12 projecting therefrom.

Finally, below labels 7 through 11, and parallel and substantially coextensive therewith, are selectors, e.g., membrane switches, 13 through 17.

All the functions designated by the labels 2 through 11 involve quantitative parameters of injection which the operator may set, preparatory to starting an injection. The settings are made by means of data entry keyboard 18 which consists essentially of a nine key alphanumeric keyboard plus a space key, a zero key, a punctuation key, a no key, a clear key, and a yes key. N.B. Each of the no, clear, and yes/enter keys also operates as a shift key, when pressed at the same time as an alphanumeric key, thereby choosing one or another of the three letters on each alphanumeric key, which if pressed alone chooses the number thereon.

For example, if one selects "X-Ray Delay", LED 12 of label 7 lights, and display 1 exhibits the current value, if any, of X-ray delay, in the bottom line of display tube 1. At this point, the operator may set X-ray delay, using keyboard 18. On the other hand, if one selects "Inject Delay", then LED 12 of label 2 lights, and display 1 exhibits the value, if any, of inject delay in the bottom line of display tube 1. At this point, the operator may set X-ray delay, using keyboard 18.

Selection of delay function is done by means of selector 13, which one presses as many times as is necessary to light the LED of the desired delay function, and at the same time, to cause the corresponding display to be exhibited on display tube 1.

Labels 2 through 11 identify more or less standard injector functions, and the selectors 13 through 17 operate to allow concentration of the ten possible indications of the values of parameters of these functions to five fields A, B, C, D and E, of display tube 1, aligned with label pairs 2 and 7, 3 and 8, 4 and 9, 5 and 10, and 6 and 11, respectively. The fields are shown as having dotted line boundaries defining them, but no such boundaries need be visible because any parameter value, when visible, will be aligned vertically with that vertical pair of labels of which one will identify the corresponding function by means of a lit LED 12. Such value will also be entirely within the confines of the zone aligned vertically with the vertical pair of labels of which one identifies the function having or being set to said value.

In addition to providing for selection between functions identified by labels, one or more of selectors 3 through 17 may provide for setting a parameter of one or more additional, but unlabeled functions. In order to utilize one or more of the selectors in this fashion, the operator presses, first, the "Special" switch at the bottom of the reference key column 19, and then, one of the selector switches, say, selector 13. This sequence causes the display tube 1 to show a set of characters which identifies an eleventh function. This set of characters, normally a phrase or two describing the function in operator-understandable language will appear in field F of the display tube 1. That is to say, field F is one of the two lines of the display, and fields A through E make up the other.

For example, it is convenient both to have a library of sets of injection parameters, preferably stored in the console, and to have a default set of injection parameters. The default injection is a set of injection parameters which is preset, that is, if the operator attempts to make an injection without having chosen one from the library, or otherwise explicitly setting the desired parameters for the injection, then upon powering up the machine it will be inherently in condition to make an injection in accordance with the default set. As will be observed from FIG. 1, no fixed label explicitly identifies a function relating to the default injection.

However, it is, of course, desirable to be able to change the default injection. To do so, one turns the machine on. The machine responds by showing in area F of display tube 1 the name, number, or other descriptor of the current default injection. In areas A, B, C, D and E will appear the values of parameters identified by labels 2 through 6. At this point, the operator may go through one or another protocol of key pressing and interaction with messages on display tube 1, designed to get the injector to a state wherein the motor 54 can actually be started by the operator, and inject according to default parameters.

Instead, the operator may want rather to change the default injection to another pre-programmed or preset default injection. Accordingly, having turned the power on and displayed the then-current default injection, the operator goes to column 20A to look up another injection, which he may do by pressing the Recall/Next switch thereof, and entering the descriptor (if he knows it) of the new default injection. (In the present case, presing recall changes the display on display tube 1 to one which offers the operator the chance to scan the library of preset injections, or to enter the description of one in particular). In any case, a new description is entered by using keyboard 18 and then pressing the Save/Enter Name switch in column 20A, and Yes in keyboard 18. As a result, display tube 1 will display the name and parameter values of the new default injection.

At this point, one may press the Special switch in column 19 and that enters the new default injection and again changes the display on display tube 1. The new display will be a menu of "special" functions, of which the default injection is one. Thus, the abbreviation DEF INJ may appear, INJ in area D and DEF directly over it in area D, i.e., each is aligned with labels 5 and 10 of select switch 16. Similarly, the abbreviated names of other special functions will be indicated at the same time in alignment with other label and select switch columns. In order to put the machine in a state to perform one of these functions, one would press the corresponding select switch. Thus, to use the default injection, one presses select switch 16, which returns the description and values of the new default injection to the display tube 1, and then goes through one of the previously mentioned protocols which, for safety reasons, are required before an injection can actually be begun.

In any event, if the machine is now turned off, then after powering up, etc., hereafter, and injecting without entering a particular set of injection parameters, the injection will be in accordance with the new default setting.

A column 20 of membrane switches provides for actually carrying out injections. For example, if a desired setting in milliliters per second has been made, or is in readiness, pressing a start switch (not shown), which may be provided, will begin the injection. Preferably, the injection continues only if the start switch is also held, (that is, once it has been pushed, releasing it will stop the injection). If the "Multiple" switch was pushed (but not held) before the enable switch was pushed, then thereafter pushing and holding the start switch will cause the injector to automatically enable the repeat of the injection. The "multiple" mode can be cleared by pushing the "Disable" switch of column 20. As indicated above, the operator preferably has to interact with the console 21 in accordance with a protocol designed to assure, as nearly as possible, safe injection before the machine will indicate injection readiness and permit the operator to make it begin.

Screen 1 is also put to use during the use of the column 20 switches. Thus, when the enable switch is pressed, the display tube 1 may display a message such as "Check the syringe for AIR", requiring the operator to press the Yes or No key of data entry keyboard 18 in order to get, respectively, either a READY TO INJECT message display tube 1, or a fault menu. Only after a READY TO INJECT message appears will pressing the start switch begin the injection.

The column 20A of membrane switches for programmed injection data control also allows, among other things, changes in the library.

Figure 2:
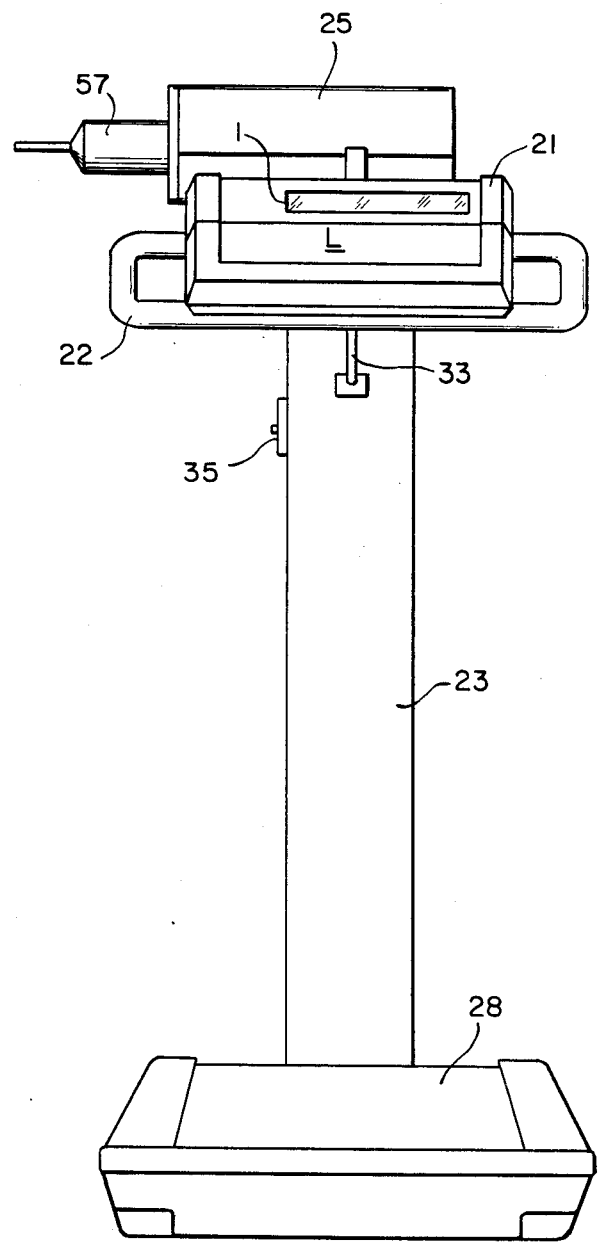
FIG. 2 is a front elevation of an injector according to the invention.
Figure 3:
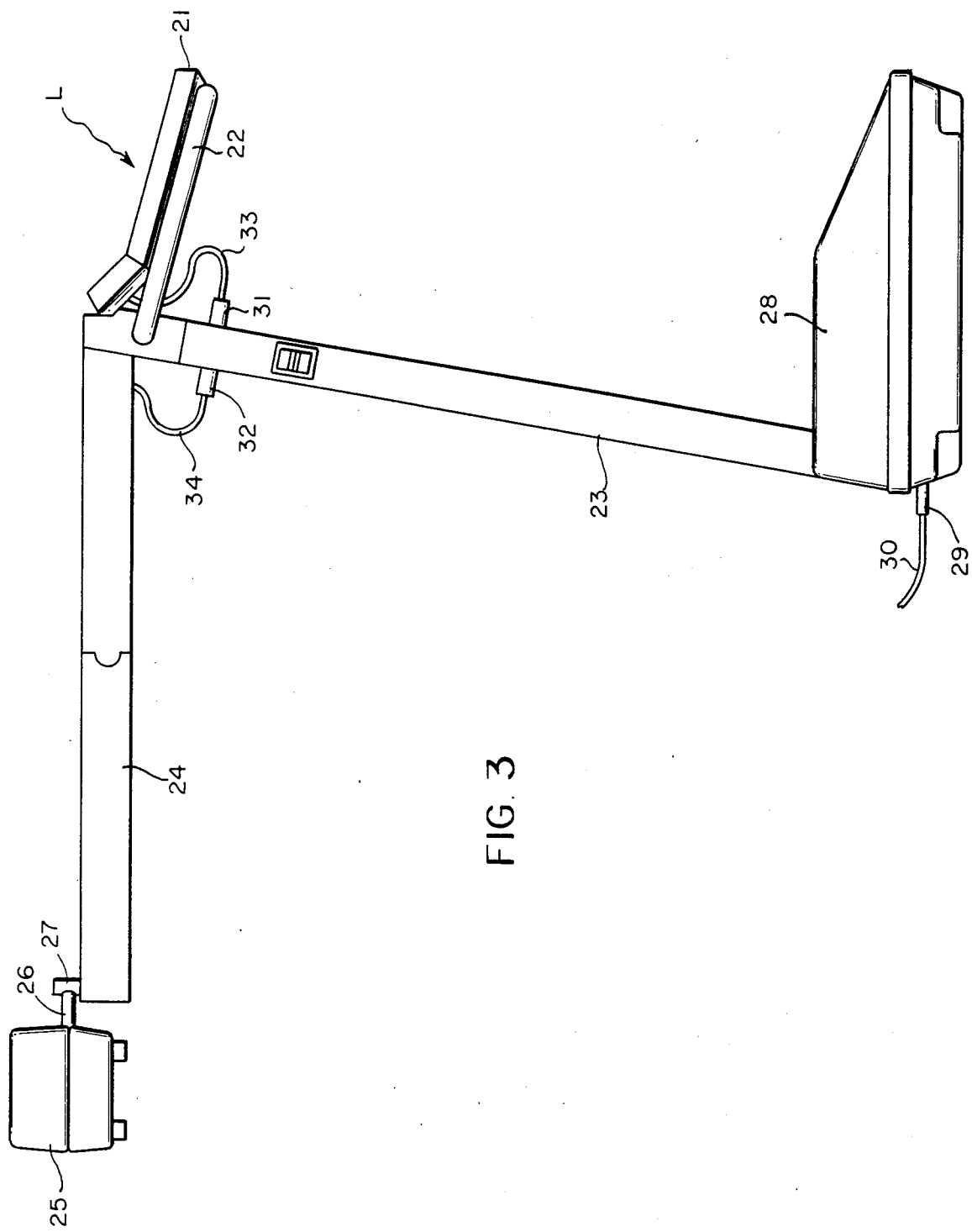
FIG. 3 is a side elevation of the injector of FIG. 2, in a different perspective.

The layout L is essentially a plan view of the top of a console 21. As shown in FIGS. 2 and 3, which for clarity do not attempt to illustrate detail of the layout L, except that display tube 1 is shown in FIG. 2, the layout L is in two intersecting planes lying at angles to the horizontal plane, with display tube 1 being the only layout element in the plane at the larger of said angles. (N.B. In FIG. 1, for ease of illustration the layout L is shown as if all in a single horizontal plane).

Console 21 is removably supported by a cradle 22, which in turn is supported on a rigid column 23. Preferably, some form of connecting device (not shown) which positively but readily-releasably secures the console to either cradle 22 or column 23, is provided. An arm 24 projecting from and supported by column 23 supports an injector head 25. Another arm 26 fixed to head 25 is rotatably received by a post 27 of arm 24. Arm 24 is articulated at its intermediate portion and at its connection to column 23, and is counterbalanced, so it and arm 26 and post 27 among them allow orienting the head at practically any location in the better part of a spherical space whose radius is a little more than the extended length of arm 24 and whose center is at the connection of arm 23. In addition, the whole is supported by a movable base 28, of sufficient mass to support head and console, regardless of head location. Preferably, base 28 has wheels, or the like, (not shown) which make it easy to move it about.

An electrical connector 29 provides for connecting the injector to the usual AC supply means, or equivalent source of electrical power, via partially-shown cord 30. Connectors 31 and 32, via cables 33 and 34, respectively connect console 21 and head 25, via the interior of column 23, to means shortly to be described, infra, there being an on-off switch 35 on column 23 for turning power from cord 30 off and on.

Cable 34 runs along arm 24, post 27 and arm 26 into the interior of head 25, there being sufficient slack provided to allow the head 25 to be freely positioned within the limits allowed by arm 24, etc., and without strain in cable 34.

The proportioning of parts, as shown, in FIGS. 2 and 3, is on the whole like that of prior art injectors we know of which are mounted on pedestals. Unlike these prior art injectors, however, the mass of the injector, and the heart of its electronics, are located in base 28. Again, like the prior art, in functioning, the injector of FIGS. 2 and 3 on the whole provides display and control of the same basic functions. Unlike the prior injectors, however, the head, on the one hand, and the display and control features, on the other hand, are physically separable from each other and from column 23, and yet remain fully operative despite such separation. Thus, one may unplug connector 31 or 32, remove console 21 or arm 24 (head 25 remaining mounting therein), mount console or arm and head elsewhere than in the immediate vicinity of base 28, and provide suitable extension cords by means of which connector 31 or 32 can be reconnected to where they originally directly connected on column 23.

Such positional separation of consoles from other injector parts was not practical with prior art injectors we know of, but is with the injector according to the invention because the cabling 33 of our injector is actually of the modest dimensions shown in FIG. 3. (N.B. while FIGS. 2 and 3 depart in some detail of configuration of existing actual injectors according to our invention, the relative proportions are shown correctly and are substantially to scale). In prior art injectors, on the other hand, such cabling of the console would have to be an order of magnitude more bulky and massive than ours, especially if, in these machines, it were attempted to provide, by conventional means, the versatility and multifariousness we have described in connection with FIG. 2 hereof. Consequently, the prior art injectors had to remain a more or less unitary assembly, insofar as the console was concerned. It is to be noted that head cabling in the prior art is light enough that the head can be separated from the injector and remain operative.

According to our invention we utilize serial data transmission both from console and from head to a computer 36 in base 28, base 28, head 25, and console 21 being shown in FIG. 4 as interconnected boxes whose relationships and functions will now be described.

Figure 4:
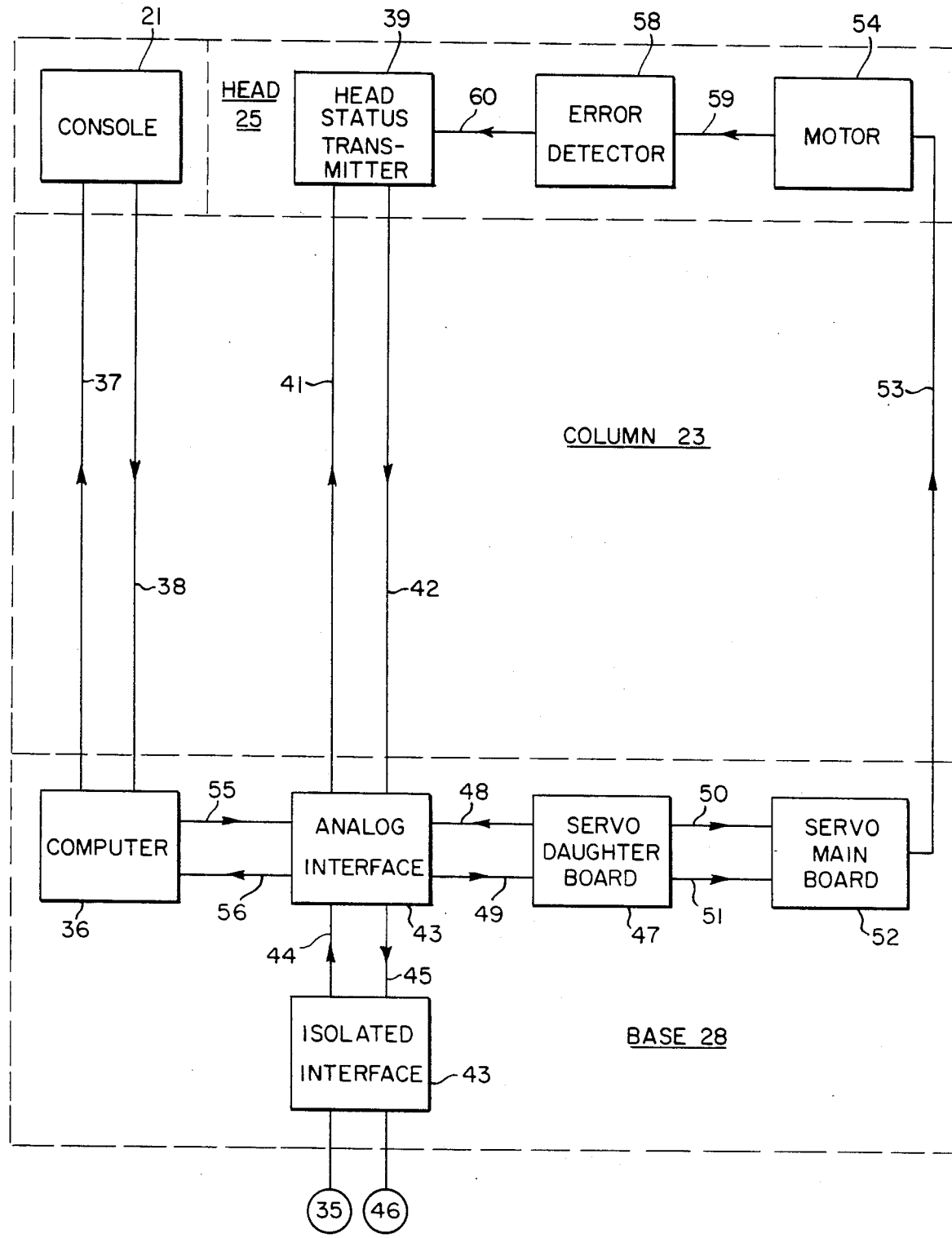
FIG. 4 is a box diagram corresponding to the injector of FIGS. 2 and 3.

In FIG. 4, the directional arrow heads on connections 37 and 38 indicate that console 21 both transmits data signals to and receives data signals from computer 36. Likewise, a head status transmitter 39 in the head 25 both transmits to and receives from an analog interface 40, also in base 28, via connections 41 and 42. An isolated interface 43 in base 28 transmits to and receives from analog interface 40 via connections 44 and 45. Isolated interface in turn, receives from switch 35 of column 23 and from foot or remote switch 46, located at any convenient place.

A servo daughter board 47 in base 28 transmits to and receives from analog interface 40 via connections 48 and 49 and in turn transmits via connections 50 and 51 to servo main board 52 in base 28 which itself transmits via connection 53 to motor 54 in head 28. Computer 36 transmits to and receives from interface 40 via connections 55 and 56.

Motor 54, of course, drives a piston (not shown) via a lead screw and reducing gear (not shown). The piston is located in a cartridge (not shown) in a jacket 57, and when driven will drive liquid in the cartridge through a catheter (not shown) dwelling in the vasculature of a living being.

Since the basic function of the injector is to dispense liquid from the cartridge in jacket 57 at a predetermined rate and/or total amount, error in one or several motor parameters are fedback to it as symbolized by the box labeled ERROR DETECTOR 58, depicted as receiving from motor 54 via connection 59 and transmitting to head status transmitter 39 via connection 60. Error detector 58 and its connections 59 and 60 are used quite generally here as representative of various known techniques for controlling injector motors by feedback of error signals representing electrically and/or mechanically manifested deviations from desired extent of piston travel, motor velocity, and so forth.

The distribution of injector connections is depicted in FIG. 4, wherein console, column head and base are symbolized by the correspondingly labeled dashed line partitioning. Since head and console are intended to be the only parts which are separable for certain uses of the injector, the physical makeup of the connections within base 28, and within head 25, the number of distinct conductors is not critical. For instance, the connections 55 and 56 may actually take the form of a fifty conductor ribbon cable.

On the other hand connections 37 and 38, 41 and 42, and 53, structurally must accommodate themselves to the cables 33 and 34 of FIG. 2. In point of fact, cable 33 has eight conductors, one pair for receiving electrical data pulses for computer 36, two pairs for transmitting electrical data pulses to computer 36, and one pair providing 5 volts D.C. or the like, for powering the console.

Similarly, cable 34 incorporates a pair of conductors for transmitting electrical data pulses to analog interface 40, a 5 volts D.C. pair for powering the head, excluding the motor 54. For powering motor 54 the connection 53 is a pair of conductors connecting the motor across a suitable source of power in the base 28.

The essential electronics of the injector is mainly in base 28. The computer 36 is based on an MC 146805E2 microprocessor manufactured by Motorola. The same microprocessor forms the electronic heart of console 21, which acts as a remote terminal for the computer 36, in that it is programmed to translate the switch pressings key strokes, etc., of the console into the appropriate displays, and for control, etc., to serially transmit switch and key stroke data signals to the computer 36 via connection 38. The computer 36 is programmed to translate this information into appropriate data signals which pass via connection 55 to the analog interface 43.

Data signals come to console 21 for display on display tube 1, some originating from computer 36 and some from elsewhere via analog interface 43, computer 36 being programmed to transmit that information serially via connection 37 to display 21.

One alternate source of information, as well as receiver of data signals is head status transmitter 39 which monitors certain conditions in the head and as well feedback information, as to motor 54, e.g., velocity and injected volume error, and sends these via serial transmission on connection 42 to analog interface 43. Analog interface 43 distributes this information to computer 36 which is programmed to assess its significance and to return, via the analog interface, appropriate data signals, representing information of various kinds, e.g., motor information is returned to the servo boards 47 and 52, as to modifying energization of the motor 54 to correct error of one kind or another.

The computer 36 is the main arbiter of how the motor is energized, and whether or not the motor runs or stops, in accordance with information resulting of diagnostic procedures, information relating to motor conditions injected volume, etc., and assessment of the operators commands, parameter settings, and observance of protocol. However, the analog interface 43 may provide for some analog data processing, and analog to digital conversion and digital to analog conversion. The mechanical elements of the head are of analog nature and function, e.g., motor energization and other motor conditions are analog, so when the computer 36 must deal with any information relating to these, the interface 43 makes the necessary D-A/A-D translation.

The console acts as a terminal for the computer 26, but it could equally well act as a terminal with a conventional, programmable "mini" or mainframe computer, because in principle such mini or mainframe could be cabled to the analog interface 43 in place of computer 26. That is to say, the combination, as such, of console 21 and computer 26, has not been described herein as performing any function which could not be performed by an appropriately programmed digital computer. In any case, conceivably the base 28 could be at a mini or mainframe installation, the injector head could be in an X-ray installation, and the console could be in an adjacent room shielded from X-radiation.

Those of ordinary skill in the art of angiography will be familiar with, or in any event, recognize the utility of the functions, etc., set forth or indicated by the layout L, FIG. 1.

For drafting convenience, some of the legendry of layout L, FIG. 1, has been abbreviated, as follows:

B.S.=Backspace
C.N.=Clear Name
Del.=Delete
Dis.=Disable
E.N.=Enter Name
En.=Enable
Ing.=Injection
Mult.=Multiple
Pat.=Patient
Prev.=Previous
Prog.=Programmed
Sel.=Select
Spec.=Special

We claim:

1. An angiographic injector for injecting liquid into the vascular system of a living being for diagnostic, therapeutic and like purposes comprising:
   a console having means operable for selecting injector functions, for setting injector parameters, and for displaying information relating to said functions and parameters into an injector head;
   a motor operated injector head for injecting said liquid into the vascular system of a living being in accordance with said preselected parameters and functions;
   a base support having means for supporting said console;
   electronic hardware for controlling said injector head in response to said means operable for selecting injector functions, for setting injector parameters, and for displaying information relating to said functions and parameters into said injector head, said hardware being located in said base support;
   means for positively securing but readily-releasing said console from said base support so as to allow said console to be readily removed from said base support and moved to a remote location for operational use.

2. The invention of claim 1, wherein said console includes serial data transmission means for transmitting signals relating to injector functions and parameter settings to the injector.

3. The invention of claim 1, wherein said injector head includes a status transmitter having serial data transmission means for transmitting signals relating to head status to said injector for display by the first said means.

4. An angiographic injector for injecting liquid into the vascular system of a living being for diagnostic, therapeutic and like purposes comprising:
   a control console having means for selecting injector functions, for setting injector parameters and for displaying information relating to said functions and parameters into an injector head;
   a motor operated injector head for injecting said liquid into the vascular system of a living being in accordance with said preselected parameters and functions;
   a base support housing;
   electronic hardware for controlling said powerhead in response to the preselected parameters selected on said console, said electronic hardware being located in said base support housing;
   a column support extending from said base support housing for supporting said console;
   means for positively securing but readily-releasing said console to said column support so as to allow said console to be readily removed from said column and moved to a remote location for operational use.

5. An angiographic injector for injecting liquid into a vascular system of a living being for diagnostic, therapeutic, and like purposes comprising a console having means for operably selecting injector functions, for selecting injector parameters, and for displaying information related to said functions and parameters into an injector head, a motor operated injector head for injecting said liquid into the vascular system of a living being in accordance with said preselected parameters and functions;
   electronic hardware means for controlling operation of said injector head in response to preselected parameter settings selected in said console, means for positively securing but readily-releasing said injector head from the remaining portion of said angiographic injector, said injector head remaining operable for injecting fluid into vascular system of a living being despite said injector head being separated from said angiographic injector, said injector head having a status transmitter having serial data transmitting means for transmitting signals to said electronic hardware means for eventual display on said console.

* * * * *